(12) United States Patent
Redler et al.

(10) Patent No.: US 6,431,219 B1
(45) Date of Patent: Aug. 13, 2002

(54) COEXTRUDED TUBING

(75) Inventors: Julie M. Redler, Encinitas; Jonathan Walborn, La Jolla; Nina Thrower, Murrieta; Leo Lopez, San Diego, all of CA (US)

(73) Assignee: ALARIS Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/777,308

(22) Filed: Feb. 5, 2001

(51) Int. Cl.[7] ............................................. F16L 11/04
(52) U.S. Cl. .................. 138/137; 138/140; 428/36.91; 604/264
(58) Field of Search ............................ 138/137, 140, 138/141; 428/36.9, 36.91, 36.6; 604/264

(56) References Cited

U.S. PATENT DOCUMENTS

| | | | |
|---|---|---|---|
| 3,034,509 A | | 5/1962 | Bernstein .................... 428/36.9 |
| 4,374,079 A | * | 2/1983 | Fouss et al. ................ 264/46.1 |
| 4,507,387 A | * | 3/1985 | Gajewski et al. .............. 435/2 |
| 4,557,959 A | | 12/1985 | Kuehlein et al. ........... 428/36.6 |
| 4,657,541 A | * | 4/1987 | Ichikawa et al. ........... 604/408 |
| 4,710,532 A | | 12/1987 | Hull et al. .................. 524/310 |
| 4,948,643 A | | 8/1990 | Mueller ................. 428/36.6 X |
| 5,274,035 A | | 12/1993 | Chundury .............. 428/36.8 X |
| 5,437,826 A | * | 8/1995 | Martinello et al. .......... 264/102 |
| 5,439,454 A | | 8/1995 | Lo et al. ...................... 604/264 |
| 5,562,127 A | * | 10/1996 | Fanselow et al. ............ 138/137 |
| 5,733,619 A | | 3/1998 | Patel et al. ............... 428/36.91 |
| 5,738,923 A | | 4/1998 | Ko et al. ................. 138/118 X |
| 5,904,967 A | | 5/1999 | Ezaki et al. ............. 138/118 X |
| 5,928,744 A | | 7/1999 | Heilmann et al. ....... 138/137 X |
| 5,932,307 A | | 8/1999 | Ryan et al. ............. 138/137 X |
| 6,004,311 A | | 12/1999 | Heilmann et al. .......... 604/533 |

OTHER PUBLICATIONS

California Environmental Protection Agency; Draft Prioritized Candidate Chemicals Under Consideration for Carninogenicity Evaluation; Sep. 24, 1997.
PDD Feature (Lisa Koval); Selecting Tubing for Medical Applications; Oct. 1997.
Rachel's Environment & Health Weekly (Environmental Research Foundation); Experimenting on Children; Jun. 18, 1998.
Bagla, Pallava, Indian Scientists Invent A Way to Safe Plastics, Indian Express Newspaper; Dec. 20, 1998.
Environmental News Service; Health Care Without Harm-;Sep. 21, 1999.
Science New; Janet Raloff; Ingredients of common plastics, may harm boys as they develop, Sep. 2, 2000, pp. 152–154, vol. 158.

* cited by examiner

*Primary Examiner*—Patrick Brinson
(74) *Attorney, Agent, or Firm*—Fulwider Patton Lee & Utecht, LLP

(57) ABSTRACT

Flexible medical grade PVC tubing has inner and outer layers coextruded with different plasticizers, with the first, inside layer of the tubing containing a plasticizer, such as di-ethylhexyl adipate, and having a thickness adapted to limit migration of a second plasticizer, such as di-ethylhexyl phthalate, from a second, outer layer of the tubing to the inside of the tubing. The flexible medical grade tubing can optionally include a third, outermost layer surrounding the second layer and containing a plasticizer such as di-ethylhexyl adipate, so that the third layer limits migration of the second plasticizer to the outside of the tubing.

24 Claims, 1 Drawing Sheet

COEXTRUDED TUBING

BACKGROUND OF THE INVENTION

This invention relates generally to materials for making medical grade products, and more particularly concerns coextruded flexible multilayer medical polyvinyl chloride (PVC) tubing with inner and outer layers coextruded with different plasticizers to provide the tubing with improved bonding properties, and to limit migration of a plasticizer in an outer layer to the inside of the tubing to minimize contact of the plasticizer with patient fluids, drugs or therapeutic agents carried in the tubing.

In the modem medical industry, medical grade tubing is commonly used to carry bodily fluids to and from patients such as in renal or blood therapies, and for delivering various drugs and therapeutic agents to patients. Such medical grade tubing is also useful in carrying patient specimens, carrier fluids and analytical agents in medical apparatus or apparatus used for medical analysis. Plastic materials are useful in forming medical grade tubing because the characteristics of the tubing can be adapted by appropriate formulation of the plastic material forming the tubing, and formation of the tubing with multiple layers having different characteristics that contribute to the desired overall characteristics of the tubing. In the formulation and construction of such medical grade tubing, it is important that such tubing be capable of being bonded with y-sites, burettes, and other devices. Other properties that may be desirable for medical grade tubing include flexibility, clarity, durability, heat resistance, strength, and the ability to shield the interior lumen of the tubing from radio waves, light or other radiation such as X-rays.

Flexible medical grade polyvinyl chloride (PVC) tubing is widely utilized due to its generally good flexibility, clarity, ease of assembly with solvent bonding, relatively low cost, and the ease of manufacturing such tubing with varying wall thicknesses and inside diameters to suit a variety of medical devices. Varying the amounts of plasticizer in the PVC formulation can be used to change the durometer or hardness and flexibility of the PVC tubing for specific applications. For example, softer, more flexible tubing can be useful in connection with parenteral infusion applications, while high durometer, less flexible, more durable PVC tubing can be more suitable for monitoring lines and medical equipment. However, some additives which contribute such desirable properties to the plastic material of the tubing may migrate from the plastic medical tubing, which may become a concern when patient bodily fluids, drugs or therapeutic agents are in contact with the tubing, such as in chronic renal dialysis when there is prolonged contact of tubing with circulating blood.

Various types of flexible, plastic, multilayer medical grade tubing are known which contain different compounds on the outside and inside of the tubing. One type of flexible medical tubing includes a coextruded multilayer medical grade tubing having an outer layer containing a polypropylene copolymer and a core formed from PVC plasticized with di-ethylhexyl phthalate (DEHP, also known as dioctyl phthalate or DOP). However, polypropylene copolymer is crystalline and difficult to solvent bond to y-sites, burettes and other devices, and migration of DEHP plasticizer from the core of the tubing can occur.

Another type of medical tubing has multiple layers formed from a soft set PVC, with a physiologically unobjectionable wall, and an adjacent physiologically questionable wall containing one or more physiologically questionable and/or untested additives. The physiologically questionable or untested additive may be one or more radiation absorbing substances which tend to migrate. This tendency to migrate is counteracted by providing a gradient of a plasticizer or softener substance such as DEHP or di-ethylhexyl adipate (DEHA, also known as dioctyl adipate, or DOA) from the physiologically unobjectionable wall to the physiologically questionable wall, which prevents migration of the questionable additive. The outer jacket of the tube of PVC is formed with a lesser amount of the plasticizer, and the inner layer of the tubing of PVC is formed with a greater amount of the plasticizer. Such a plasticizer gradient between two layers of PVC is undesirable because it makes one layer softer than the other, and can cause the tubing to peel apart or kink. With a greater amount of plasticizer in the inner jacket of the tubing, the inner jacket becomes softer, so that the inner softer jacket of the tubing can become thinned, pinched, or cut through when the tubing is pinched, for example with a pinch type clamp such as a C-clamp.

While PVC with DEHP plasticizer is readily bondable to y-sites, burettes and other devices, it may be desirable to limit direct contact of DEHP with patient fluids, drugs or therapeutic agents. While DEHA can be used as a PVC plasticizer, it is difficult to bond PVC with DEHA plasticizer to other devices, so that stronger solvents are required to attain bonding of such tubing with other devices, which is undesirable. DEHA also chemically reacts with styrene based materials, such as polystyrene, so that bonding of PVC with DEHA plasticizer can eventually result in bond failure, because the DEHA can weaken the styrene material as well as the bonded joint over time.

One type of medical grade tubing has a multilayer structure not containing PVC, avoiding the use of any PVC plasticizers altogether. However, since PVC has proved to be such an extremely versatile and useful plastic, it would be desirable to provide a flexible medical grade PVC tubing utilizing DEHP, which is a useful and otherwise desirable PVC plasticizer, in a configuration that would limit migration and direct contact of DEHP with patient fluids, drugs or therapeutic agents, and that provides improved bonding properties to the flexible medical grade PVC tubing. The present invention meets these and other needs.

SUMMARY OF THE INVENTION

Briefly, and in general terms, the present invention provides for a flexible medical grade PVC tubing with inner and outer layers coextruded with different plasticizers to provide improved bonding properties to the tubing, and limited migration of plasticizer in an outer layer of the tubing to the inside of the tubing. The flexible medical grade PVC tubing is useful for carrying fluids, drugs and therapeutic agents.

The present invention accordingly provides for a flexible medical grade tubing having coextruded first and second layers. The first layer is formed of PVC containing a first plasticizer, and forms an innermost layer of the tubing. The second layer surrounds the first layer, and is formed of PVC containing a second plasticizer different from the first plasticizer. The second plasticizer in the second layer provides valuable properties to the characteristics of the tubing, and the first layer with the first plasticizer limits migration of the second plasticizer to the inside of the tubing. In a presently preferred embodiment, the first layer can be dimensioned to have a thickness sufficient to limit migration of the second plasticizer to the inside of the tubing to a desired level. In a presently preferred embodiment, the first plasticizer is di-ethylhexyl adipate (DEHA). The second plasticizer is preferably a plasticizer that contributes desired characteristics and improved bonding properties to the medical tubing. In one presently preferred embodiment, the second plasticizer is di-ethylhexyl phthalate (DEHP).

In a presently preferred embodiment, the second layer forms the outermost layer of the tubing. In an alternate embodiment, the flexible medical grade tubing can optionally include a third layer surrounding the second layer and containing a plasticizer different from the second plasticizer, such as di-ethylhexyl adipate (DEHA). The third layer can have a thickness dimensioned sufficient to limit migration of the second plasticizer to the outside of the tubing to a desired level. The third layer can optionally form the outermost layer of the tubing.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
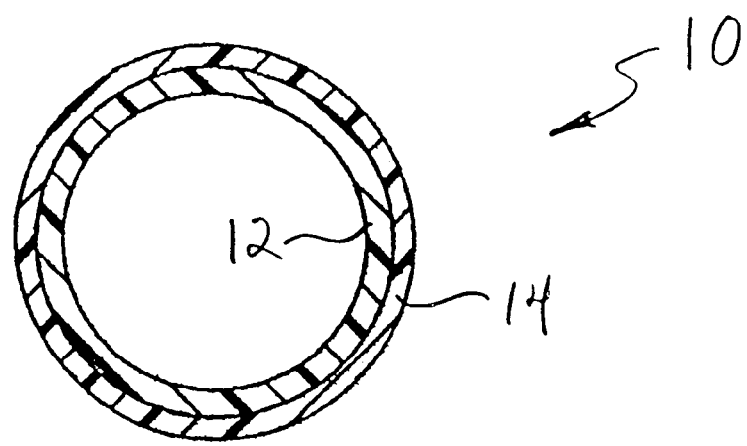
FIG. 1 is a cross-sectional view of the flexible medical grade tubing of the invention.

It is important for medical grade tubing to have good bonding properties for bonding with y-sites, burettes and other devices, and it can be important for medical grade tubing, such as that used for supplying medical fluids to a patient, to minimize the risk of exposing the patient to substances that can migrate from the tubing to the medical fluids. Particularly with medical grade PVC tubing, it may be desirable to limit the migration to the inside of the tubing of additives, such as DEHP, that can otherwise be useful in PVC tubing to provide the medical grade PVC tubing with useful bonding properties.

As is illustrated in the drawings, the invention is embodied in a flexible medical grade PVC tubing with inner and outer layers coextruded with different plasticizers, in order to provide desired characteristics and improved bonding properties to the medical tubing, with the layers of the tubing arranged and dimensioned to limit migration of a plasticizer in an outer layer of the tubing to the inside of the tubing.

Referring to FIG. 1, in a first presently preferred embodiment, the invention provides for a flexible medical grade tubing 10 having multiple layers that can be produced by coextrusion of the tubing to form a first, innermost layer 12 and a second, outer layer 14 surrounding the first layer. Coextrusion and consequent thermal bonding of the layers can be accomplished by joining one or more smaller extruders to a main extruder to produce the layers of tubing desired. The first, innermost layer is currently preferably formed of PVC containing a first plasticizer, such as di-ethylhexyl adipate (DEHA). The thickness of the first, innermost layer of tubing can be adjusted as needed to limit the migration of a second plasticizer in one or more outer layers of the tubing to the inside of the tubing to less than or equal to a desired level. While DEHA is presently preferred as the plasticizer used in the innermost layer of the PVC tubing, other plasticizers, such as phthalates, other adipates, azelates, phosphates, maleates, epoxidized vegetable oil, derivatives and combinations thereof and the like may also be suitable.

The second, outer layer surrounding the first layer is also preferably formed of PVC, but contains a second plasticizer different from the first plasticizer that can provide improved bonding characteristics to the tubing, such as di-ethylhexyl phthalate (DEHP), that can migrate from the tubing. While DEHP is currently preferred as the plasticizer utilized in the outer layer of the PVC tubing, other plasticizers that can provide improved bonding characteristics to the tubing, such as diisononyl phthalate (DINP), other phthalates, adipates, azelates, phosphates, maleates, derivatives and combinations thereof and the like, may also be useful in the second layer. In a preferred embodiment, the second layer forms the outermost layer of the tubing. In this embodiment, the tubing can be used in medical equipment or for supplying medical fluids to a patient to limit exposure of the patient to the plasticizer in the outer layer through the medical fluids delivered to the patient, because medical fluids carried within the tubing will be separated and protected from the outer layer of the tubing by the innermost layer of the tubing. In addition, the plasticizers in the first and second layers are preferably provided in similar amounts so that the first and second layers do not differ substantially in softness.

The preferred overall tubing thickness is about 0.015 to 0.060 inch, although the overall tubing thickness is typically 0.020 inch. The outer diameter of the tubing is preferably about 0.080 to 0.165 inch, although the outer diameter of the tubing is typically 0.145 inch. The first, innermost layer 12 is preferably in the range of about 1/4 to 3/4 of the overall tubing thickness, and is typically 0.006 inch thick. Due to manufacturing limitations, the first layer is preferably no less than about 0.004 inch. The second, outer layer 14 surrounding the first layer is preferably in the range of about 3/4 to 1/4 of the overall tubing thickness, and is typically no less than about 0.004 inch thick. The thickness of the layers also depends upon how much plasticizer is in the layers, and the resultant softness of the layers.

Figure 2:
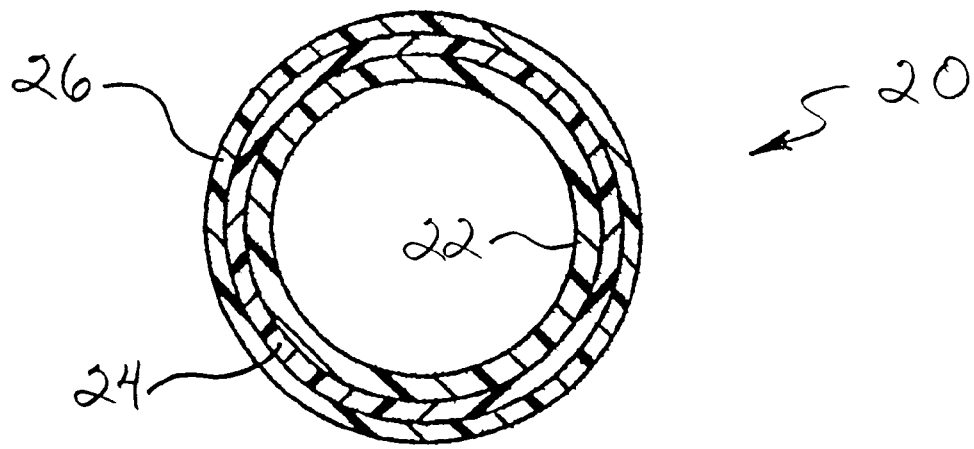
FIG. 2 is a cross-sectional view of an alternative embodiment of the flexible medical grade tubing of the invention.

In another presently preferred embodiment illustrated in FIG. 2, the invention provides for a flexible medical grade tubing 20 having multiple layers that can be produced by coextrusion of the tubing to bond the multiple layers together to form a first, innermost layer 22 formed of PVC containing a first plasticizer, such as DEHA. The thickness of the first, innermost layer of tubing can be adjusted as needed to limit the migration of a second plasticizer in an outer layer of the tubing to the inside of the tubing to be less than or equal to an acceptable level. While DEHA is presently preferred as the plasticizer used in the innermost layer of the PVC tubing, other plasticizers, such as phthalates, other adipates, azelates, phosphates, maleates, epoxidized vegetable oil, derivatives and combinations thereof and the like, may also be useful in the first layer.

A second layer 24 surrounding the first layer is also preferably formed of PVC, but contains a second plasticizer different from the first plasticizer that can provide improved bonding characteristics to the tubing, such as di-ethylhexyl phthalate (DEHP), that can migrate from the tubing. While DEHP is currently preferred as the plasticizer utilized in the second layer of the PVC tubing, other plasticizers that can provide improved bonding characteristics to the tubing such as DINP, other phthalates, adipates, azelates, phosphates, maleates, derivatives and combinations thereof and the like, may also be useful in the second layer. In this embodiment, the tubing includes a third layer 26 surrounding the second layer that is preferably the outermost layer, and that contains a plasticizer that is different from the second plasticizer, and that has a thickness that can be adjusted as needed to limit migration of the plasticizer from the second layer to be less than or equal to a desired level. In a presently preferred embodiment, the plasticizer in the third layer is DEHA. The plasticizer of the third layer may alternatively be selected from other plasticizers, such as phthalates, other adipates, azelates, phosphates, maleates, epoxidized vegetable oil, derivatives and combinations thereof and the like, as noted above. Fluids carried within the tubing will be separated and protected from plasticizer in the second layer of the tubing by the innermost layer of the tubing. The outermost layer can additionally limit migration of the plasticizer in the second layer to the outside of the tubing by adjusting the thickness of the third layer as needed, to protect the patient and others from contact with plasticizer from the second layer. In addition, the plasticizers in the multiple layers are preferably provided in similar amounts so that the multiple layers do not differ substantially in softness.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A flexible medical grade tubing having coextruded multiple layers, comprising:
   a first layer formed of polyvinyl chloride containing a first plasticizer, said first layer forming an innermost layer of the tubing; and
   a second layer surrounding said first layer formed of polyvinyl chloride containing a second plasticizer different from said first plasticizer.

2. The flexible medical grade tubing of claim 1, wherein said first layer limits migration of said second plasticizer to the inside of the tubing.

3. The flexible medical grade tubing of claim 1, wherein said first plasticizer is di-ethylhexyl adipate.

4. The flexible medical grade tubing of claim 1, wherein said second layer comprises an outermost layer of the tubing.

5. The flexible medical grade tubing of claim 1, wherein said second plasticizer is di-ethylhexyl phthalate.

6. The flexible medical grade tubing of claim 1, further comprising a third layer surrounding said second layer and containing a plasticizer different from said second plasticizer, and wherein said third layer limits migration of said second plasticizer to the outside of the tubing.

7. The flexible medical grade tubing of claim 6, wherein said plasticizer in said third layer is di-ethylhexyl adipate.

8. The flexible medical grade tubing of claim 6, wherein said third layer comprises an outermost layer of the tubing.

9. A coextruded flexible medical grade tubing having inner and outer layers for supplying medical fluids to a patient and limiting exposure of the patient to an additive in the outer layer, the flexible medical grade tubing comprising:
   an inner layer formed of polyvinyl chloride containing a first plasticizer; and
   an outer layer surrounding said inner layer formed of polyvinyl chloride containing a second plasticizer different from said first plasticizer.

10. The coextruded flexible medical grade tubing of claim 9, wherein said first layer has a thickness adapted to limit migration of said second plasticizer to the inside of the tubing to a desired level.

11. The coextruded flexible medical grade tubing of claim 9, wherein said first plasticizer is di-ethylhexyl adipate.

12. The coextruded flexible medical grade tubing of claim 9, wherein said second plasticizer is di-ethylhexyl phthalate.

13. A coextruded flexible medical grade tubing having inner and outer layers for supplying medical fluids to a patient and limiting exposure of the patient to an additive in an outer layer, the flexible medical grade tubing comprising:
   an inner layer formed of polyvinyl chloride containing a first plasticizer; and
   at least one outer layer surrounding said inner layer formed of polyvinyl chloride containing a second plasticizer different from said first plasticizer, and wherein said first layer has a thickness adapted to limit migration of said second plasticizer to the inside of the tubing to a desired level.

14. The coextruded flexible medical grade tubing of claim 13, wherein said first plasticizer is di-ethylhexyl adipate.

15. The coextruded flexible medical grade tubing of claim 13, wherein said second plasticizer is di-ethylhexyl phthalate.

16. The flexible medical grade tubing of claim 1 wherein the tubing has a generally circular cross-section.

17. The flexible medical grade tubing of claim 16 wherein said first layer limits migration of said second plasticizer to the inside of the tubing.

18. The flexible medical grade tubing of claim 16 wherein said first plasticizer comprises di-ethylhexyl adipate.

19. The flexible medical grade tubing of claim 16 wherein said second layer comprises an outermost layer of the tubing.

20. The flexible medical grade tubing of claim 16 wherein said second plasticizer comprises di-ethylhexyl phthalate.

21. The flexible medical grade tubing of claim 9 wherein the tubing has a generally circular cross-section.

22. The coextruded flexible medical grade tubing of claim 21 wherein said first layer has a thickness adapted to limit migration of said second plasticizer to the inside of the tubing to a desired level.

23. The coextruded flexible medical grade tubing of claim 21 wherein said first plasticizer comprises di-ethylhexyl adipate.

24. The coextruded flexible medical grade tubing of claim 21 wherein said second plasticizer comprises di-ethylhexyl phthalate.

* * * * *